United States Patent [19]

Böhner et al.

[11] 3,992,398

[45] Nov. 16, 1976

[54] PROCESS FOR THE PRODUCTION OF 1,2,4-TRIAZOLE DERIVATIVES

[75] Inventors: Beat Böhner, Binningen; Dag Dawes, Muttenz; Willy Meyer, Riehen, all of Switzerland; Jean Perchais, Rixheim, France; Hanspeter Fischer, Bottmingen, Switzerland

[73] Assignee: Ciba-Geigy Corporation, Ardsley, N.Y.

[22] Filed: June 3, 1975

[21] Appl. No.: 583,377

[30] Foreign Application Priority Data

June 13, 1974 Switzerland.......................... 8088/74
Dec. 6, 1974 Switzerland....................... 16244/74

[52] U.S. Cl. .......................... 260/308 R; 260/308 C; 260/583 B
[51] Int. Cl.² ........................................ C07D 249/12
[58] Field of Search .................... 260/308 R, 308 C

[56] References Cited

UNITED STATES PATENTS

| | | | |
|---|---|---|---|
| 3,701,784 | 10/1972 | Seidel et al. .................... | 260/308 R |
| 3,755,349 | 8/1973 | Timmler et al. ................ | 260/308 R |
| 3,862,125 | 1/1975 | Hoffmann et al. .............. | 260/308 C |

OTHER PUBLICATIONS

Elderfield, Heterocyclic Compounds, vol. 8, (New York, 1961), pp. 425–426.

Schulze, J. Prakt. Chem., Vierte Reihe, Band 26, pp. 268–271.

Jensen et al., Acta. Chem. Scand., vol. 22, pp. 1–50, (1968).

*Primary Examiner*—Alton D. Rollins
*Attorney, Agent, or Firm*—Karl F. Jorda; Frederick H. Rabin

[57] ABSTRACT

Process for the production of 1-alkyl-3-hydroxy-5-chloro-1,2,4-triazoles wherein an alkylhydrazine is reacted in an inert solvent in the presence of an acid binding agent with cyanogen chloride to 1-alkyl-1-cyanohydrazine which is subsequently cyclized with phosgene.

12 Claims, No Drawings

PROCESS FOR THE PRODUCTION OF 1,2,4-TRIAZOLE DERIVATIVES

The present invention relates to a process for the production of 1-alkyl-3-hydroxy-5-chloro-1,2,4-triazoles of the formula

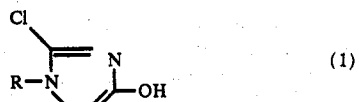

wherein R represents a straight-chain or branched-chain alkyl group having 1 to 5 carbon atoms.

The 1-alkyl-3-hydroxy-5-chloro-1,2,4-triazoles of the above formula are valuable intermediates for the production of pesticides. They can be converted by, in particular, reaction with phosphoric acid ester halides and thiophosphoric acid ester halides into phosphoric acid esters and thiophosphoric acid esters, respectively, which have an excellent insecticidal action. Such compounds are described in the Belgian Pat. No. 792,452.

The production of 1-alkyl-3-hydroxy-5-chlor-1,2,4-triazoles of formula I starting from hydrazine, by conversion into semicarbazide, into a corresponding semicarbazone, hydrogenation thereof to give alkyl-semicarbazide, cyclization with orthoformic acid ester to 1-alkyl-3-hydroxy-1,2,4-triazole and subsequent chlorination thereof in the 5-position, is known. On account of the large number of steps required, this process is very complicated, and is furthermore not satisfactory also with regard to the attainable yields.

It has now been found that 1-alkyl-3-hydroxy-5-chloro-1,2,4-triazoles of formula I can be produced in a simple manner by a process in which an alkylhydrazine of formula II $$R - NH - NH_2 \quad (II)$$

wherein R has the meaning given under formula I, or a salt of such an alkylhydrazine, is firstly reacted, in the presence of an acid-binding agent, with cyanogen chloride to the corresponding 1-alkyl-1-cyanohydrazine, and this is subsequently cyclized with phosgene to a 1-alkyl-3-hydroxy-5-chloro-1,2,4-triazole of formula I.

Suitable salts of an alkylhydrazine of formula II used as starting material are, for example, the hydrochloride, the sulphate, the oxalate and the acetate.

Inorganic and organic bases are suitable as acid-binding agents, such as, e.g., alkali metal hydroxides and alkaline-earth metal hydroxides, alkali metal bicarbonates and alkaline-earth metal bicarbonates and alkali metal carbonates and alkaline-earth metal carbonates, as well as tertiary amines such as trialkylamines, dialkylanilines, pyridines and picolines.

The process according to the invention is performed advantageously in an inert solvent. Identical or different solvents can be used for the reaction with cyanogen chloride and for the cyclization with phosgene. Suitable solvents are, e.g., aliphatic and aromatic hydrocarbons or halogenated hydrocarbons, such as hexane, petroleum ether, chloroform, methylene chloride, halogenated ethanes, benzene, toluene, xylene, ethers and ethereal compounds such as dialkyl ether, 1,2-dimethoxyethane, dioxane, tetrahydrofuran, N,N-dialkylated amides such as dimethylformamide, sulphoxides such as dimethylsulphoxide, nitriles such as acetonitrile, ketones such as acetone and methyl ethyl ketone. For the reaction of an alkylhydrazine of formula II with cyanogen chloride, it is possible to use as solvent also water or a mixture of water with an organic solvent, e.g. an alcohol.

It is advantageous to perform the reaction of an alkylhydrazine of formula II with cyanogen chloride in a halogenated lower alkane, e.g. methylene chloride or chloroform, or in a halogenated ethane. The solvent used for this reaction may also be a mixture of ethanol and water.

Solvents that have proved particularly suitable for the cyclization of 1-alkyl-1-cyanohydrazine with phosgene are methylene chloride and dioxane. If the same solvent is employed for the reaction of alkylhydrazine with cyanogen chloride and for cyclization with phosgene, then isolation of 1-alkyl-1-cyanohydrazine, which is formed as intermediate, can be dispensed with.

The reaction of the alkylhydrazines of formula II with cyanogen chloride is performed at a temperature of between −20° and 80° C, preferably between −5° C and 30° C. The subsequent cyclization of 1-alkyl-1-cyanohydrazine with phosgene can be carried out at a temperature of between 0° and 180° C, preferably between 20° and 130° C.

According to a preferred embodiment of the process of the invention, the 1-alkyl-3-hydroxy-5-chloro-1,2,4-triazoles of formula I are isolated as hydrochlorides from the reaction mixture. Particularly pure products are obtained in this manner.

By means of the process suggested according to the invention, it becomes possible to produce 1-alkyl-3-hydroxy-5-chloro-1,2,4-triazoles of formula I from hydrazine in four reaction steps, whereas five are necessary with use of the known process initially mentioned. Furthermore, the yields obtained with the process according to the invention are higher than those obtained with the known process.

The process according to the invention is further illustrated by the following examples.

EXAMPLE 1 a. 1-Cyano-1-isopropylhydrazine 2000 ml of methylene chloride and 228 g of sodium carbonate are added successively to a solution of 221 g of isopropylhydrazine hydrochloride in 500 ml of water. Into the two-phase system thus obtained there is introduced at 5°–10° C, in the course of 40 minutes, 123 g of cyanogen chloride, with carbon dioxide being given off; after about 15 hours, there is no further formation of carbon doxide. The mixture is filtered, the methylene chloride phase is separated, and the aqueous layer is again extracted, in this case with 200 ml of methylene chloride. After the methylene chloride phases have been evaporated off, there is obtained crude 1-cyano-1-isopropylhydrazine as a liquid residue, which is purified by distillation (b.p. 100°–101° C/9 Torr).

b. 1-Isopropyl-3-hydroxy-5-chloro-1,2,4-triazole

Into 100 ml of toluene there is introduced at 0°–5° C, within 15 minutes, 10 g of phosgene. An addition is made dropwise to this solution, within 15 minutes, of a solution of 10 g of 1-cyano-1-isopropylhydrazine in 20 ml of toluene. HCl gas is then fed in during 3 seconds, and the temperature is raised within 1 hour to 50° C. After 5 hours at 50° C, 3 g of phosgene is introduced and the mixture is maintained for a further hour at 50° C. After cooling of the mixture, the toluene phase is distilled off and the residue is treated with water/toluene at 40°–50° C. This operation is repeated with the water phase, and the toluene phases containing triazole are concentrated by evaporation. The resulting crude triazole is purified by recrystallisation from water to obtain 1-isopropyl-3-hydroxy-5-chloro-1,2,4-triazole, m.p. 104°–106° C.

EXAMPLE 2

1-Isopropyl-3-hydroxy-5-chloro-1,2,4-triazole hydrochloride

A solution of 19.4 g of 1-cyano-1-isopropylhydrazine in 30 ml of dioxane is added dropwise, in the course of 25 minutes, to a solution of 25 g of phosgene in 120 ml of dioxane, with the internal temperature being maintained between 10° and 15° C. After 15 minutes, the temperature is allowed to rise to 25° C, whereupon the formed 1-isopropyl-3-hydroxy-5-chloro-1,2,4-triazole hydrochloride commences to precipitate. After several hours, the precipitate is filtered off and dried. There is obtained 23 g of 1-isopropyl-3-hydroxy-5-chloro-1,2,4-triazole hydrochloride, m.p. 138°–142° C. From the filtrate there is obtained, by removal of the solvent by evaporation in vacuo, a further 8 g of 1-isopropyl-3-hydroxy-5-chloro-1,2,4-triazole hydrochloride. Total yield = 31 g, corresponding to 79.5% of theory.

EXAMPLE 3

Into a solution of isopropylhydrazine hydrochloride in a mixture of 3 parts of water and one part of alcohol there is introduced, at a temperature of 10° C, an equivalent amount of cyanogen chloride, with a pH-range of 6.5 to 7 being maintained by addition of sodium hydroxide solution and checking with a pH-meter. The duration of the reaction is 1 hour. During the reaction, there precipitates a yellow oil from which there is obtained, by extraction with ether, the crude 1-isopropyl-cyano-hydrazine in a yield of 90% as oil. The crude product obtained in this way can be used directly for the further reaction with phosgene to give 1-isopropyl-3-hydroxy-1,2,4-triazole.

The crude 1-isopropyl-1-cyanohydrazine can be purified by column chromatography on silica gel 60,70 to 230 mesh (Merck). After eluting with ether, there is obtained pure 1-isopropyl-1-cyanohydrazine.

Into a solution of 1-isopropyl-1-cyanohydrazine in toluene there is introduced at 10° C an equivalent amount of phosgene, whereupon there precipitates a clear yellow resin which does not go into solution even on subsequent boiling up of the reaction mixture. This clear yellow resin consists to the extent of 30% of 1-isopropyl-3-hydroxy-5-chloro-1,2,4-triazole. To determine the content of 1-isopropyl-3-hydroxy-5-chloro-1,2,4-triazole, a specimen of the resin is dissolved by boiling it in dioxane, and is then chromatographed on a DC finished plate (silica gel 60) with toluene/glacial acetic acid (4:1). The chromatogram is developed with iodine. The RF-value of 1-isopropyl-3-hydroxy-5-chloro-1,2,4-triazole is 0.6. Authentic 1-isopropyl-3-hydroxy-5-chloro-1,2,4-triazole, m.p. 100°–104° C, gives under identical conditions the same RF-value.

EXAMPLE 4 a. 1-sec.Butyl-1-cyanohydrazine

To 300 g of hydrazine hydrate there are added dropwise, with ice cooling, firstly 460 g of methyl ethyl ketone and subsequently 1200 g of concentrated hydrochloric acid. The resulting acidified solution of methyl ethyl ketone hydrazone is hydrogenated, after the addition thereto of 10 g of catalyst (5% platinum on charcoal), at normal pressure with hydrogen to give 1-sec.butylhydrazine. After absorption of 120 liters of hydrogen, the catalyst is filtered off, and 680 g of solid sodium hydroxide is added with ice cooling to the filtrate. The mixture obtained after the addition of 1000 ml of methylene chloride is then transferred to a sulphonating flask provided with cooling apparatus, thermometer and stirrer. There is then introduced, with ice cooling and stirring, 365 g of cyanogen chloride in the course of 2 hours. After 2 hours' subsequent stirring, the precipitated salt is filtered off, and washed with an amount of methylene chloride. The organic phase is afterwards separated and the aqueous phase is extracted twice with 300 ml of methylene chloride. The methylene chloride solutions are combined and the methylene chloride is evaporated off in vacuo. By distillation of the oily residue, there is obtained 417 g (62% of theory) of 1-sec.butyl-1-cyanohydrazine (boiling point 72° C/11 mm).

b. 1-sec.Butyl-3-hydroxy-5-chloro-1,2,4-triazole

A solution of 22.6 g of 1-sec.butyl-1-cyanohydrazine in 30 ml of dioxane is added dropwise at room temperature, during 15 to 20 minutes, to a solution of 25 g of phosgene in 120 ml of dioxane. After completion of the addition, there is added 1 g of active charcoal and the reaction mixture is refluxed for 3 hours. After cooling to room temperature, 10 g of sodium bicarbonate is added. After 15 hours, the mixture obtained is filtered through Hyflo for removal of the salts. The filtrate is concentrated at 70° C in vacuo, with 31.5 g of a brown oil remaining. After the addition of a solution of 8 g of sodium hydroxide in 50 ml of water, the whole is heated for 15 minutes at 90° C. After cooling to room temperature, the mixture is extracted with 75 ml of ether. After separation of the ether, the aqueous phase is neutralised with 100 ml of 2N hydrochloric acid, whereupon 1-sec.butyl-3-hydroxy-5-chloro-1,2,4-triazole precipitates firstly as oil, which coon crystallises. There is obtained 23 g (65.5% of theory) of 1-sec.butyl-3-hydroxy-5-chloro-1,2,4-triazole, m.p. 77°–79° C.

There is obtained in an analogous manner, starting with methylhydrazine, 1-methyl-1-cyanohydrazine, b.p. 73° C/0.3 mm; and from this, by reaction with phosgene, 1-methyl-3-hydroxy-5-chloro-1,2,4-triazole, m.p. 154° C (decomposition).

EXAMPLE 5

25.5 kg of 30% sodium hydroxide solution (corresponding to 191 moles of NaOH) is added, with brine cooling and continuous stirring, to 20 kg of a 33% aqueous solution of isopropylhydrazine hydrochloride containing 6.6 kg (60 moles) of isopropylhydrazine hydrochloride, in the course of which the internal temperature is not allowed to exceed 15° C. An addition is subsequently made of 25 kg of methylene chloride, and there is then introduced, within 3 hours, 3.9 kg (63 moles) of cyanogen chloride, with the internal temperature being always kept below 15° C. The aqueous phase is then separated, and extracted twice with 30 kg of methylene chloride. The methylene chloride solutions are combined and the methylene chloride is evaporated off in vacuo. The yield is 5.7 g (96.5% of theory) of crude 1-isopropyl-1-cyanohydrazine.

EXAMPLE 6

A solution of 30 g of 1-isopropyl-1-cyanohydrazine in 45 ml of methylene chloride is added dropwise, in the course of 5 hours, to a solution, cooled to 5° C, of 59 g of phosgene in 180 ml of methylene chloride. After completion of the addition, the temperature is allowed to rise to room temperature, and stirring is maintained for 24 hours, with 1-isopropyl-3-hydroxy-5-chloro-1,2,4-triazole precipitating out in crystalline form as hydrochloride. There is obtained 33 g (53.2% of theory) of 1-isopropyl-3-hydroxy-5-chloro-1,2,4-triazole hydrochloride, m.p. 138°–142° C.

There can be obtained from the mother liquor, after extraction with diluted sodium hydroxide solution and removal of the methylene chloride by evaporation, a further 8.2 g (16.9% of theory) of crude 1-isopropyl-3-hydroxy-5-chloro-1,2,4-triazole, m.p. 99°–104° C.

We claim:

1. Process for the production of 1-alkyl-3-hydroxy-5-chloro-1,2,4-triazoles of formula I

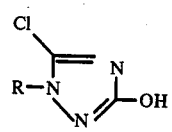

wherein
R represents a straight-chain or branched-chain alkyl group having 1 to 5 carbon atoms,
in which process an alkylhydrazine of formula II

wherein R has the meaning given under formula I, or a salt of such an alkylhydrazine, is firstly reacted, in the presence of an acid-binding agent, with cyanogen chloride to the corresponding 1-alkyl-1-cyanohydrazine, and this is subsequently cyclized with phosgene to a 1-alkyl-3-hydroxy-5-chloro-1,2,4-triazole of formula I.

2. Process according to claim 1, wherein the employed salt of an alkylhydrazine of formula II is the hydrochloride, the sulphate, the oxalate or the acetate.

3. Process according to claim 1, wherein the acid-binding agent used is an alkali metal hydroxide or alkaline-earth metal hydroxide, an alkali metal bicarbonate or alkaline-earth metal bicarbonate or an alkali metal carbonate or alkaline-earth carbonate, or a tertiary amine.

4. Process according to claim 1, wherein the reactions are performed in the presence of an inert solvent.

5. Process according to claim 1, wherein the reaction of an alkylhydrazine of formula II with cyanogen chloride is performed in a halogenated lower alkane.

6. Process according to claim 1, wherein the reaction of an alkylhydrazine of formula II with cyanogen chloride is performed in methylene chloride.

7. Process according to claim 1, wherein the cyclization of a 1-alkyl-1-cyanohydrazine with phosgene is performed in methylene chloride or in dioxane.

8. Process according to claim 1, wherein the reaction of an alkylhydrazine of formula II with cyanogen chloride is performed at a temperature of between −20° and 80° C.

9. Process according to claim 1, wherein the cyclization of a 1-alkyl-1-cyanohydrazine with phosgene is performed at a temperature of between 0° and 180° C.

10. Process according to claim 1, wherein the 1-alkyl-3-hydroxy-5-chloro-1,2,4-triazoles of formula I are isolated as hydrochlorides from the reaction mixture.

11. Process according to claim 8, wherein the reaction of an alkyl hydrazine of formula II with cyanogen chloride is performed at a temperature between −5° and 30° C, inclusive.

12. Process according to claim 9, wherein the cyclization is performed at a temperature between 20° and 130° C, inclusive.

* * * * *